United States Patent
Caspers

(10) Patent No.: US 6,974,484 B2
(45) Date of Patent: Dec. 13, 2005

(54) OSMOTIC MEMBRANE AND VACUUM SYSTEM FOR ARTIFICIAL LIMB

(75) Inventor: Carl A. Caspers, Avon, MN (US)

(73) Assignee: Otto Bock Healthcare LP, Minneapolis, MN (US)

( * ) Notice: Subject to any disclaimer, the term of this patent is extended or adjusted under 35 U.S.C. 154(b) by 0 days.

(21) Appl. No.: 11/044,133

(22) Filed: Jan. 27, 2005

(65) Prior Publication Data

US 2005/0131549 A1  Jun. 16, 2005

Related U.S. Application Data

(63) Continuation of application No. 09/829,306, filed on Apr. 9, 2001, now abandoned, which is a continuation-in-part of application No. 09/325,297, filed on Jun. 3, 1999, now abandoned, and a continuation-in-part of application No. 09/534,274, filed on Mar. 23, 2000, now Pat. No. 6,554,868.

(51) Int. Cl.[7] .............................................. A61F 2/80
(52) U.S. Cl. ......................................... 623/34; 623/32
(58) Field of Search ............................. 623/27, 33–37, 623/57

(56) References Cited

U.S. PATENT DOCUMENTS

| | | | |
|---|---|---|---|
| 2,424,278 A | 7/1947 | Kunkel |
| 2,606,325 A | 8/1952 | Nielson |
| 2,664,572 A | 1/1954 | Blevens |
| 2,671,225 A | 3/1954 | Schoene |
| 2,696,011 A | 12/1954 | Galdik |
| 3,253,600 A | 5/1966 | Scholl |
| 3,322,873 A | 5/1967 | Hitchcock |
| 3,377,416 A | 4/1968 | Kandel |
| 3,393,407 A | 7/1968 | Kandel |
| 3,557,387 A | 1/1971 | Ohlenbusch |
| 3,631,542 A | 1/1972 | Potter |
| 3,712,298 A | 1/1973 | Snowdon |
| 3,732,578 A | 5/1973 | Pollack |
| 3,751,733 A | 8/1973 | Fletcher |
| 3,858,379 A | 1/1975 | Graves |
| 3,895,405 A | 7/1975 | Edwards |
| 3,975,350 A | 8/1976 | Hudgin |
| 3,991,424 A | 11/1976 | Prahl |
| 4,314,398 A | 2/1982 | Pettersson |
| 4,381,768 A | 5/1983 | Erichsen |
| 4,404,296 A | 9/1983 | Schapel |

(Continued)

FOREIGN PATENT DOCUMENTS

AU  670631  7/1996

(Continued)

OTHER PUBLICATIONS

Solomons, Organic Chemistry (6th ed,), John Wiley & Sons, Inc., New York, 1996 pp. 853-854.

(Continued)

*Primary Examiner*—Corrine McDermott
*Assistant Examiner*—William H Matthews
(74) *Attorney, Agent, or Firm*—Faegre & Benson, LLP

(57) ABSTRACT

A system for removing perspiration from a residual limb inserted in a prosthesis comprising an nonporous prosthesis socket, a porous thin sheath adjacent the socket, a nonporous liner adjacent the sheath, an osmotic membrane adjacent the liner allowing water vapor to pass from the limb but preventing liquid from passing to the limb, a nonporous seal that prevents air leakage between the residual limb and the socket; and, a vacuum source to reduce the pressure in a space between the limb and socket. A method of removing perspiration from a residual limb in a prosthesis.

14 Claims, 3 Drawing Sheets

U.S. PATENT DOCUMENTS

| | | | |
|---|---|---|---|
| 4,456,642 | A | 6/1984 | Burgdorfer |
| 4,466,936 | A | 8/1984 | Schapel |
| 4,479,272 | A | 10/1984 | Beldzisky |
| 4,623,354 | A | 11/1986 | Childress |
| 4,634,446 | A | 1/1987 | Kristensson |
| 4,635,626 | A | 1/1987 | Lerman |
| 4,704,129 | A | 11/1987 | Massey |
| 4,822,371 | A | 4/1989 | Jolly |
| 4,828,325 | A | 5/1989 | Brooks |
| 4,888,829 | A | 12/1989 | Kleinerman |
| 4,908,037 | A | 3/1990 | Ross |
| 4,923,475 | A | 5/1990 | Gosthnian |
| 5,007,937 | A | 4/1991 | Fishman |
| 5,108,455 | A | 4/1992 | Telikicherla |
| 5,133,776 | A | 7/1992 | Crowder |
| 5,139,523 | A | 8/1992 | Paton |
| 5,211,667 | A | 5/1993 | Danforth |
| 5,221,222 | A | 6/1993 | Townes |
| 5,258,037 | A | 11/1993 | Caspers |
| 5,314,497 | A | 5/1994 | Fay et al. |
| 5,362,834 | A | 11/1994 | Schapel |
| 5,376,131 | A | 12/1994 | Lenze |
| 5,376,132 | A | 12/1994 | Caspers |
| 5,507,834 | A | 4/1996 | Laghi |
| 5,534,034 | A | 7/1996 | Caspers |
| 5,549,709 | A | 8/1996 | Caspers |
| 5,571,208 | A | 11/1996 | Caspers |
| 5,593,454 | A | 1/1997 | Helmy |
| 5,658,353 | A | 8/1997 | Layton |
| 5,702,489 | A | 12/1997 | Slemker |
| 5,728,167 | A | 3/1998 | Lohmann |
| 5,728,168 | A | 3/1998 | Laghi |
| 5,728,169 | A | 3/1998 | Norvell |
| 5,728,170 | A | 3/1998 | Becker |
| 5,735,906 | A | 4/1998 | Caspers |
| 5,888,216 | A | 3/1999 | Haberman |
| 5,888,230 | A | 3/1999 | Helmy |
| 5,888,231 | A | 3/1999 | Sandvig |
| 5,904,721 | A | 5/1999 | Henry et al. |
| 5,904,722 | A | 5/1999 | Caspers |
| D429,335 | S | 8/2000 | Caspers et al. |
| 6,231,617 | B1 | 5/2001 | Fay |
| 6,273,918 | B1 | 8/2001 | Yuhasz et al. |
| 6,287,345 | B1 | 9/2001 | Slemker et al. |
| 6,508,842 | B1 | 1/2003 | Caspers |
| 6,554,868 | B1 | 4/2003 | Caspers |
| 6,645,253 | B2 | 11/2003 | Caspers |
| 6,726,726 | B2 | 4/2004 | Caspers |
| 6,761,742 | B2 | 7/2004 | Caspers |
| 2001/0016781 | A1 | 8/2001 | Caspers |
| 2004/0024322 | A1 | 2/2004 | Caspers |
| 2004/0030411 | A1 | 2/2004 | Caspers |
| 2004/0098136 | A1 | 5/2004 | Caspers |
| 2004/0143345 | A1 | 7/2004 | Caspers |
| 2004/0163278 | A1 | 8/2004 | Caspers |
| 2004/0167638 | A1 | 8/2004 | Caspers |
| 2004/0181290 | A1 | 9/2004 | Caspers |

FOREIGN PATENT DOCUMENTS

| | | | |
|---|---|---|---|
| BE | 675386 | | 5/1966 |
| CA | 2098945 | | 7/1997 |
| DE | 745981 | | 5/1944 |
| DE | 2712342 | | 9/1977 |
| DE | 3221920 | | 6/1982 |
| DE | 4217877 | | 12/1992 |
| DE | 9419211 | | 3/1995 |
| DE | 9417913 | | 4/1995 |
| DE | 29905020 | | 7/1999 |
| EP | 0057839 | | 8/1982 |
| EP | 0086147 | A | 8/1983 |
| EP | 0057838 | | 3/1985 |
| EP | 0261884 | | 3/1988 |
| EP | 0320170 | | 6/1989 |
| EP | 0363654 | | 4/1990 |
| EP | 0631765 | | 1/1995 |
| EP | 0650708 | | 5/1995 |
| EP | 0870485 | | 10/1998 |
| FR | 1135516 | | 9/1960 |
| FR | 1532625 | | 7/1968 |
| FR | 2420335 | | 10/1979 |
| FR | 2501999 | | 3/1981 |
| GB | 136504 | | 1/1920 |
| GB | 267988 | | 3/1927 |
| GB | 2069847 | | 9/1981 |
| GB | 2149309 | | 6/1985 |
| JP | 7155343 | | 6/1995 |
| SU | 1771722 | | 10/1992 |
| SU | 1812982 | | 4/1993 |
| SU | 1821177 | A1 | 6/1993 |
| WO | WO 95/05792 | | 3/1995 |
| WO | WO 96/21405 | | 7/1996 |
| WO | WO 98/55055 | | 12/1998 |
| WO | WO 99/65434 | | 12/1999 |
| WO | WO 00/03665 | | 1/2000 |
| WO | WO 00/74611 | A2 | 12/2000 |
| WO | WO 01/54631 | | 2/2001 |

OTHER PUBLICATIONS

Sympatex Technologies GmbH Data Sheets (5 pgs.).
SealSkinz Web Page (4 pgs.).
Gore-Tex Web Page (2 pgs.).
Gill Web Page (2 pgs.).

OSMOTIC MEMBRANE AND VACUUM SYSTEM FOR ARTIFICIAL LIMB

CROSS-REFERENCE TO RELATED APPLICATION

This is a continuation of U.S. patent application Ser. No. 09/829,306, filed on Apr. 9, 2001, now abandoned which is a continuation-in-part of U.S. patent application Ser. No. 09/325,297, filed Jun. 3, 1999, now abandoned, and U.S. patent application Ser. No. 09/534,274, filed Mar. 23, 2000, issued as U.S. Pat. No. 6,554,868.

BACKGROUND OF THE INVENTION

The present invention relates to prosthetic devices and more particularly to a hypobarically-controlled artificial limb for amputees and to a method for removing perspiration from the space between the residual limb and the liner by means of an osmotic membrane and an applied vacuum.

An amputee is a person who has lost part of an extremity or limb such as a leg or arm which commonly may be termed as a residual limb. Residual limbs come in various sizes and shapes with respect to the stump. That is, most new amputations are either slightly bulbous or cylindrical in shape while older amputations that may have had a lot of atrophy are generally more conical in shape. Residual limbs may further be characterized by their various individual problems or configurations including the volume and shape of a stump and possible scar, skin graft, bony prominence, uneven limb volume, neuroma, pain, edema or soft tissue configurations.

Referring to FIGS. 1 and 2, a below the knee residual limb 10 is shown and described as a leg 12 having been severed below the knee terminating in a stump 14. In this case, the residual limb 10 includes soft tissue as well as the femur 16, knee joint 18, and severed tibia 20 and fibula 22. Along these bone structures surrounded by soft tissue are nerve bundles and vascular routes which must be protected against external pressure to avoid neuromas, numbness and discomfort as well as other kinds of problems. A below the knee residual limb 10 has its stump 14 generally characterized as being a more bony structure while an above the knee residual limb may be characterized as including more soft tissue as well as the vascular routes and nerve bundles.

Referring to FIG. 2, amputees who have lost a part of their arm 26, which terminates in a stump 28 also may be characterized as having vascular routes, nerve bundles as well as soft and bony tissues. The residual limb 10 includes the humerus bone 30 which extends from below the shoulder to the elbow from which the radius 34 and ulna 36 bones may pivotally extend to the point of severance. Along the humerus bone 30 are the biceps muscle 38 and the triceps muscle 40 which still yet may be connected to the radius 34 and the ulna, 36, respectively.

In some respects, the residual limb amputee that has a severed arm 26 does not have the pressure bearing considerations for an artificial limb but rather is concerned with having an artificial limb that is articulable to offer functions typical of a full arm, such as bending at the elbow and grasping capabilities. An individual who has a paralyzed limb would also have similar considerations wherein he or she would desire the paralyzed limb to having some degree of mobility and thus functionality.

During the day, as the residual limb amputee walks on an artificial limb, perspiration builds up between the residual limb and the liner which cushions the residual limb in the artificial limb socket. As this perspiration buildup continues, the residual limb begins to slip around within the liner, causing a feeling to the wearer of losing contact with the artificial limb. This slippage often also causes irritation to the residual limb, which may be worsened by a growth of bacteria in the warm, moist environment between the residual limb and the liner.

There is a need for an improved hypobarically-controlled artificial limb that will offer total contact relationship with the residual limb; absorb and dissipate shock, mechanical and shear forces typically associated with ambulation, twisting and turning and weight bearing with an artificial limb; control residual limb volume by way of even weight distribution; use negative pressure as a locking device to hold the residual limb into the socket without causing swelling of the residual limb into the socket; and control the buildup of perspiration on the residual limb. One of the ways of controlling the buildup of perspiration is to use a vacuum system to wick away this perspiration from the residual limb.

U.S. Pat. No. 5,888,230 discloses the use of a vacuum pump connected between the limb and a liner. However, this invention is essentially inoperable because the liner will conform to the stump at all times, by an interference fit, so that there is no space between the residual limb and the liner against which to draw a vacuum. In any case, the patent does not disclose application of vacuum to the socket cavity in such a manner as to draw the residual limb firmly and totally against the interior of the socket. Instead, the patent discloses the use of shims between the liner and the socket. Without total contact between the residual limb and the socket, the limb may swell into the space between the limb and the socket. Also, the patent does not disclose the use of vacuum to remove perspiration.

U.S. Pat. No. 5,549,709 discloses several embodiments of a hypobarically-controlled artificial limb. However, all of these embodiments required two sockets: an outer socket and an inner socket. Applicant has found that the present invention offers improved performance without the requirement for two sockets. A single socket works equally well or better than two sockets. Also, this patent does not disclose a mechanism for maintaining vacuum in the presence of air leakage into the socket.

It has been found that it is essentially impossible to maintain a perfect, airtight seal between the residual limb and the sockets disclosed in U.S. Pat. No. 5,549,709, with the result that slow air leakage into the sockets diminishes the vacuum in the sockets. With the reduction in vacuum, the beneficial effects of the vacuum also slowly diminish. Consequently, there is a need for a means for maintaining the vacuum in the socket cavity in the presence of some air leakage past the seal.

SUMMARY OF THE INVENTION

A system for removing perspiration from a residual limb inserted in a prosthesis comprising an nonporous prosthesis socket, a porous thin sheath adjacent the socket, a nonporous liner adjacent the sheath, an osmotic membrane adjacent the liner allowing water vapor to pass from the limb but preventing liquid from passing to the limb, a nonporous seal that prevents air leakage between the residual limb and the socket; and a vacuum source to reduce the pressure in a space between the limb and socket.

A method of removing perspiration from a residual limb in a prosthesis comprising the steps of inserting the residual limb into a sleeve comprising an osmotic membrane that allows water vapor to pass from the limb but prevents liquid from passing to the limb. The residual limb and osmotic membrane sleeve are inserted into a flexible, nonporous liner. The residual limb, osmotic membrane sleeve, and liner are inserted into a porous sheath. The residual limb, osmotic membrane sleeve, liner, and sheath are inserted into a prosthetic socket cavity having a volume and shape to receive the residual limb. The socket cavity is sealed with a nonporous seal, and vacuum applied to the socket cavity in the space between the membrane and the socket to draw the residual limb and liner into firm contact with the socket and provide a reduced pressure in the socket cavity.

DESCRIPTION OF THE PREFERRED EMBODIMENT

Figure 1:
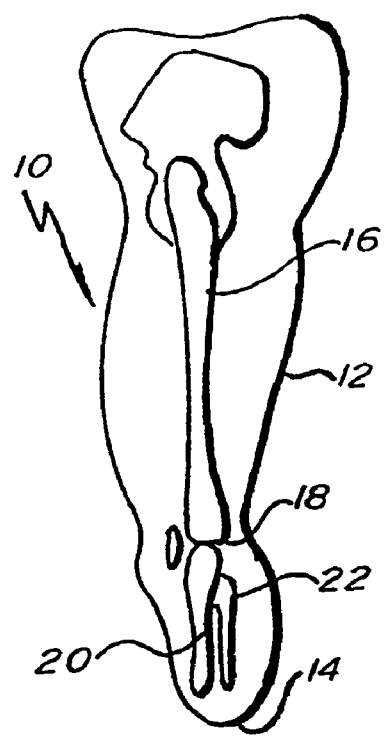
FIG. 1 is a side elevational view of the tissue and skeletal structure of an amputee's residual limb.
Figure 2:
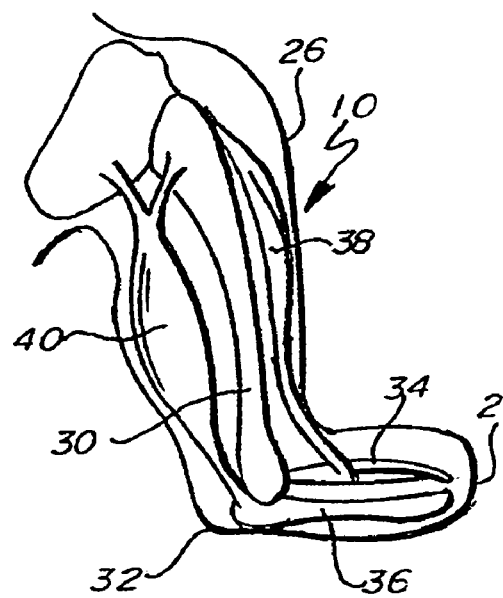
FIG. 2 is a side elevational view of a residual limb in the form of an amputated arm showing the skeletal and muscular structure of the residual limb.
Figure 3:
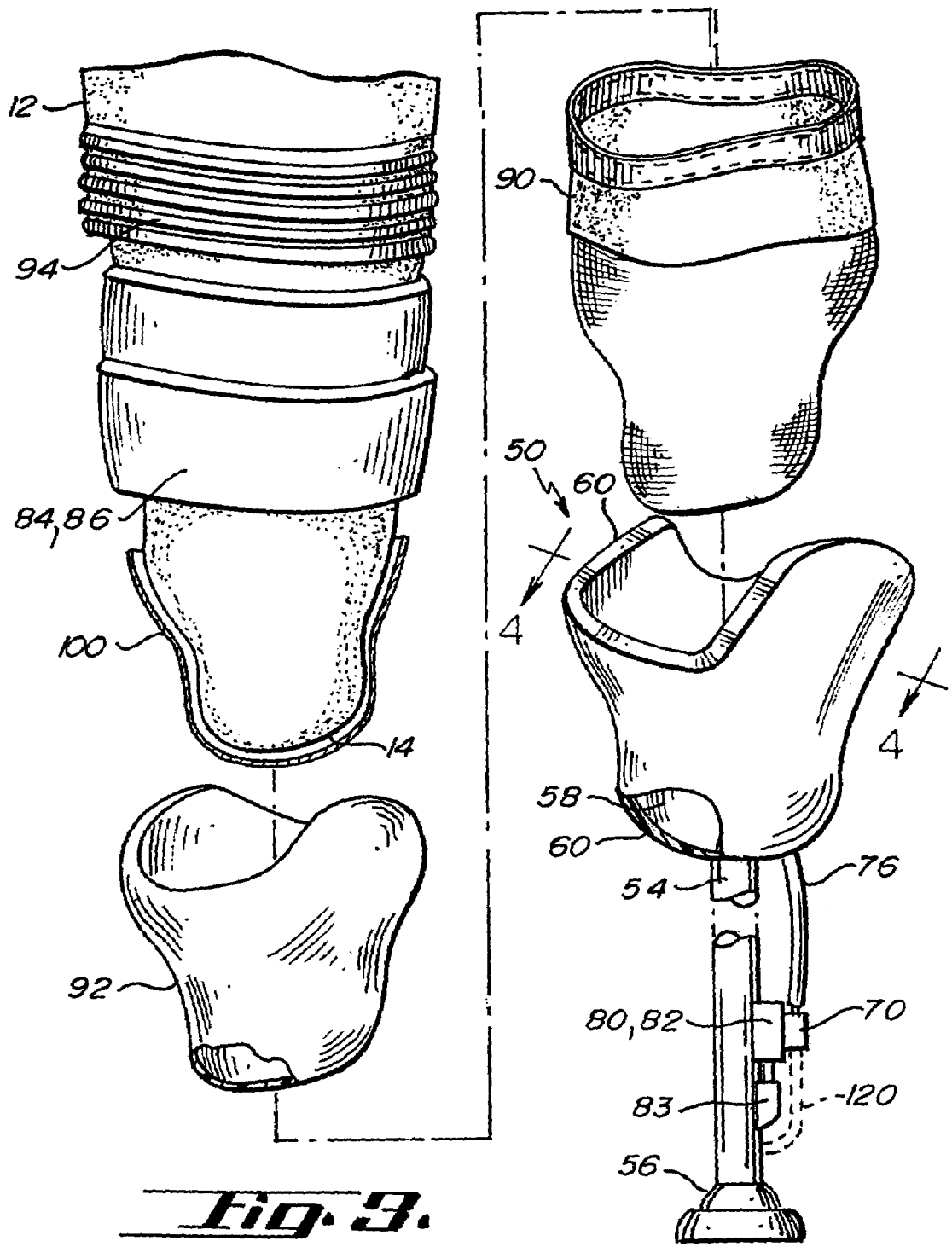
FIG. 3 is an exploded elevational view of the residual limb donning the polyurethane sleeve, stretchable nylon sleeve, liner, osmotic membrane, nylon sheath and socket of an artificial limb.
Figure 4:
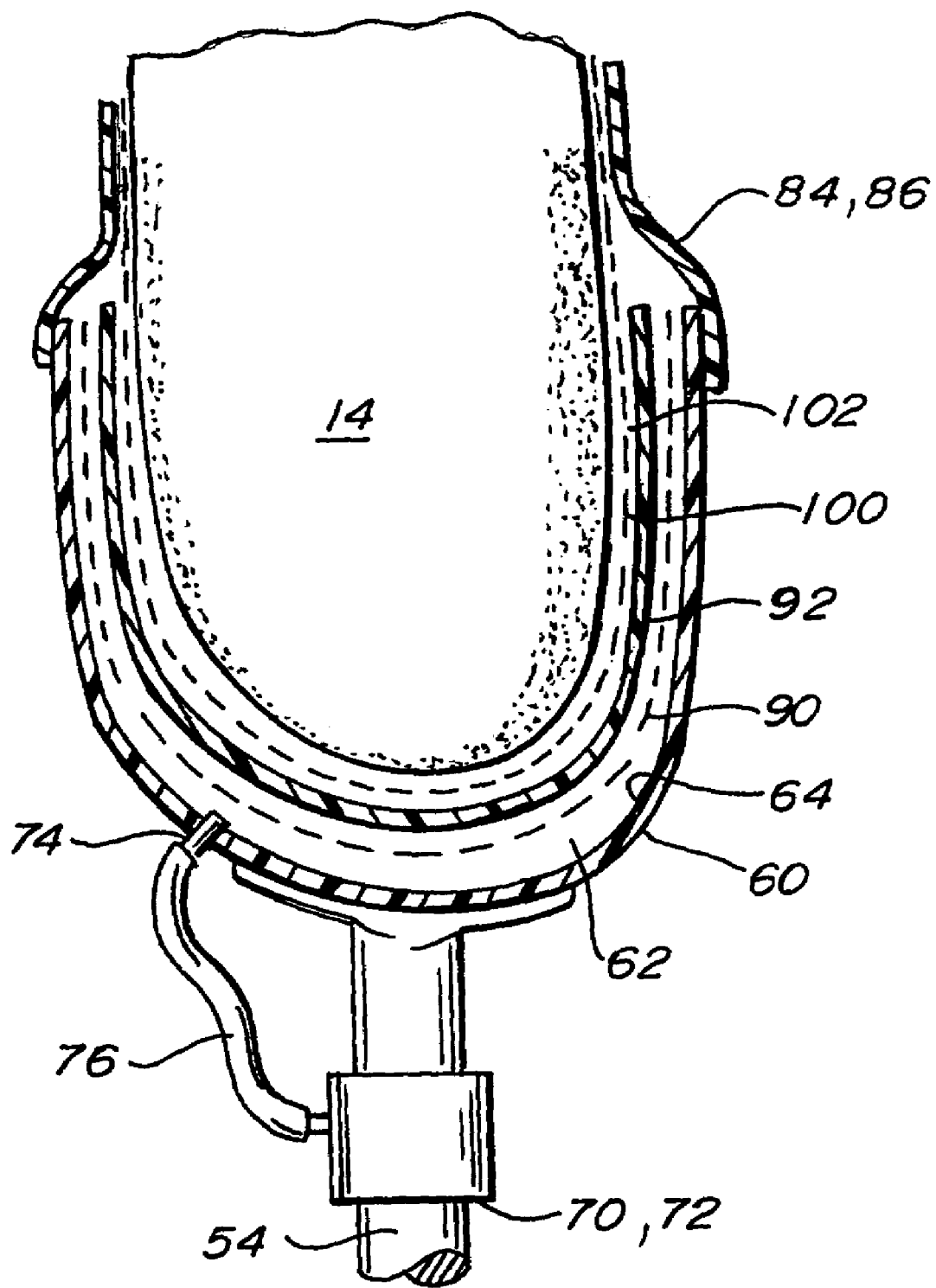
FIG. 4 is a cross-section along the lines 4 of FIG. 3.

FIGS. 3 and 4 show one embodiment of the apparatus 50 of the present invention. The hypobarically-controlled artificial limb 50 includes a single socket 60, shin 54, and foot 56. The socket 60 has a volume and shape to receive a substantial portion of the residual limb 14 with a space 58 therebetween.

The apparatus 50 further includes a cavity 62 in the socket 60 with a volume and shape for receiving a substantial portion of the residual limb 14.

A vacuum source 70 may conveniently be attached to the shin or pylon 54. The vacuum source 70 may preferably be a mechanical or motor-driven pump 72. The vacuum source 70 may be connected to a power source 83, which may be a battery.

A vacuum valve 74 is suitably connected to the vacuum source 70. The vacuum valve 74 may preferably be disposed on the socket 60. A vacuum tube 76 connects the vacuum valve 74 to the cavity 62. It will be seen that the vacuum source will cause the residual limb 14 to be drawn into firm contact with the inner surface 64 of the socket 60.

The hypobarically-controlled artificial limb 50 also includes a regulator means 80 for controlling the vacuum source 70. Preferably, the regulator means 80 may be a digital computer 82. Alternately, the regulator means may be a vacuum regulator. The regulator means 80 is connected to a power source 83, which may be a battery.

A seal means 84 makes an airtight seal between the residual limb 14 and the socket 60. Preferably, the seal means 84 is a nonfoamed, nonporous polyurethane suspension sleeve 86 which rolls over and covers the socket 60 and a portion of the residual limb 14. Alternatively, the seal means 84 may be any type of seal which is airtight.

The apparatus 50 may also include a nonfoamed, nonporous polyurethane liner 92 receiving the residual limb 14 and disposed between the socket 60 and the residual limb 14. The liner 92 provides a total-contact hypobaric suction, equal weight distribution socket liner. The liner 92 readily tacks up to the skin of the residual limb 14 and provides total contact with the limb 14. The liner 92 absorbs and dissipates shock, mechanical and shear forces typically associated with ambulation.

The hypobarically-controlled artificial limb 50 may also include a thin sheath 90 between the liner 92 and the inner surface 64 of the socket 60. As vacuum is applied to the cavity 62, the sheath 90 will allow the vacuum to be evenly applied throughout the cavity 62. Without the sheath 90, the liner 92 might "tack up" against the inner surface 64 and form a seal which might prevent even application of the vacuum to the cavity 62. The sheath 90 may also be used to assist the amputee into a smooth and easy fitting into the inner socket 60. The sheath 90 is preferably made of thin knitted nylon.

The hypobarically-controlled artificial limb 50 may also include a stretchable nylon second sleeve 94 for rolling over and covering the suspension sleeve 86 to prevent clothing from sticking to and catching the suspension sleeve 86.

The hypobarically-controlled artificial limb 50 may also include an osmotic membrane 100 encompassing the residual limb 14 and creating a space 102 between the residual limb 14 and the liner 92. The osmotic membrane 100 allows perspiration to pass in one direction only from the residual limb outward toward the liner 92.

This beneficial effect of the osmotic membrane is achieved as follows. The osmotic membrane allows water vapor to pass through the membrane from the side of the membrane with a higher partial water vapor pressure (the residual limb side) to the side of the membrane with a lower partial water vapor pressure (the liner side), but not in the opposite direction. Eventually, the partial water vapor pressure on the two sides of the osmotic membrane would become equal, and transmission of vapor through the membrane would cease. However, application of vacuum to the space 102 will continually lower the partial water vapor pressure on the liner side of the membrane 100, so that water vapor will continue to pass through the membrane. In turn, this lowers the partial water vapor pressure on the residual limb side of the membrane 100, allowing perspiration on the residual limb to change from the liquid state to the vapor state.

Appropriate materials for the osmotic membrane 100 are the Sympatex hydrophylic polyester block copolymer from Sympatex Technologies, One Merrill Industrial Drive, Suite 201, Hampton, N.H. 03842; the Goretex® material from A.W. Gore & Associates, www.gore.com; the Gill 02 Fabric from Gill North America, 1025 Parkway Industrial Park, Buford, Ga. 30581; and the SealSkinz product from Porvair, Estuary Road, King's Lynn, Norfolk, PE30 2HS, United Kingdom.

The osmotic membrane may be laminated onto a supporting fabric, such as a cloth stump sock.

An important aspect of the osmotic membrane 100 is that it should have no pores into which the skin of the residual limb 14 may be drawn under the influence of vacuum.

Optionally, vacuum from the vacuum source may be applied to the space 102 between the osmotic membrane 100 and the liner 92. Application of vacuum lowers the boiling point of water, allowing perspiration passing through the osmotic membrane 100 to evaporate and be removed from the space 102.

Referring to FIG. 3, the polyurethane tubular sleeve 86 may be appreciated alone and in combination with the urethane liner 92 together with the optional nylon sheath 90 and second stretchable nylon sleeve 94.

More specifically, the amputee takes the stretchable nylon second sleeve 94, suitably made of a spandex-like material and rolls it up over the stump 14 to the upper portions of the residual limb suitably as the thigh of a leg 12. Next, the polyurethane sleeve 86 is also rolled upwardly over the residual limb 10. The amputee than places the osmotic membrane 100 over the residual limb 14. Thereafter, the liner 92 is donned.

Next, the amputee may optionally utilize the nylon sheath 90 which is suitably of a non-stretching, thin, friction reducing nylon. As stated, this sheath 90 optionally may be used to assist the amputee into a smooth and easy fitting into the socket 60. Alternatively, the sheath 90 may be avoided and the liner 92 simply inserted into the socket 60 of the artificial limb 50.

Next, the amputee simply grasps the rolled over portion of the polyurethane sleeve 86 and rolls it over a substantial portion of the socket 60. The sleeve 86 makes an airtight seal between the residual limb 14 and the socket 60.

As can be appreciated, the polyurethane sleeve 86 is tacky. Consequently, the stretchable nylon second sleeve 94 may be utilized and rolled over the polyurethane sleeve 86.

The amputee then sets the regulator means 80 to cause the vacuum source 70 to apply vacuum through the vacuum valve 74 and vacuum tube 76 to the cavity 62. Enough vacuum is applied to cause the residual limb (with optional coverings) to be drawn firmly against the inner surface 64 of the socket 60, which is flexible. The vacuum source 70 may preferably maintain a vacuum in the range of 0 to 25 inches of mercury (ideally ten to twenty five inches).

It will be seen that the vacuum within the socket 60 will cause the hypobarically-controlled artificial limb 50 to be suspended from the residual limb 14. The vacuum will lock the residual limb 14 into the socket 60 without causing swelling of the residual limb into the socket, because of the total contact of the residual limb 14 with the socket 60. That is, there is no open chamber between the residual limb 14 and the socket 60 which would draw on the residual limb.

As the volume of the residual limb 14 decreases during the day due to weight-bearing pressures, the regulator means 80 may appropriately adjust the vacuum source 70 to draw the residual limb 14 more firmly against the socket 60 and thus compensate for the loss of residual limb volume. The vacuum may also partially or completely oppose the loss of fluids from the residual limb caused by weight-bearing pressures.

The vacuum within the socket 60 is also applied to the space 102 between the osmotic membrane 100 and the liner 92. Application of vacuum to the space 102 lowers the boiling point of water, causing perspiration wicking through the osmotic membrane to evaporate and be drawn out of the space 102.

The vacuum source 70 may be a weight-actuated vacuum pump and shock absorber as disclosed in U.S. patent application Ser. No. 09/534,274, filed Mar. 23, 2000 and herein incorporated by reference.

To maintain the vacuum in the cavity, either a regulator means 80, or a weight-actuated vacuum pump and shock absorber as disclosed in U.S. patent application Ser. No. 09/534,274, may be employed.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A system for removing perspiration from a residual limb inserted in a prosthesis comprising:
   a nonporous prosthesis socket;
   a porous thin sheath adjacent the socket;
   a nonporous liner adjacent the sheath;
   an osmotic membrane adjacent the liner allowing water vapor to pass from the limb but preventing liquid from passing to the limb;
   a nonporous seal that prevents air leakage between the residual limb and the socket; and
   a vacuum source to reduce the pressure in a space between the limb and socket.

2. The system of claim 1 wherein the nonporous seal is a nonfoamed, nonporous polyurethane suspension sleeve.

3. The system of claim 1, wherein the vacuum source is a vacuum pump, a regulator and a power source.

4. The system of claim 1, wherein the vacuum source is a weight-actuated vacuum pump.

5. The system of claim 1, where in the sheath is a porous, knitted nylon material.

6. The system of claim 1, wherein the liner is nonfoamed, nonporous polyurethane.

7. A method of removing perspiration from a residual limb in a prosthesis comprising the steps of:
   inserting the residual limb into a sleeve comprising an osmotic membrane that allows water vapor to pass from the limb but preventing liquid from passing to the limb;
   inserting the residual limb and osmotic membrane sleeve into a flexible, nonporous liner;
   inserting the residual limb, osmotic membrane sleeve and liner into a porous sheath;
   inserting the residual limb, osmotic membrane sleeve, liner and sheath into a prosthetic socket cavity having a volume and shape to receive the residual limb;
   sealing the socket cavity with a nonporous seal; and
   applying a vacuum to the socket cavity in the space between the membrane and the socket to draw the residual limb and liner into firm contact with the socket and provide a reduced pressure in the socket cavity.

8. The method of claim 7, further comprising the step of maintaining the vacuum in the socket cavity, in the presence of some air leakage into the socket cavity.

9. The method of claim 7, wherein the sheath is a porous knitted nylon material.

10. The method of claim 7, wherein the liner is of a nonfoamed, nonporous polyurethane.

11. The method of claim 7, wherein the nonporous seal is nonfoamed, nonporous polyurethane suspension sleeve.

12. The method of claim 7, wherein the vacuum source is a vacuum pump, a regulator and a power source.

13. The method of claim 7, wherein the vacuum source is a weight-actuated vacuum pump.

14. The method of claim 7, wherein a vacuum of at least ten inches of mercury is maintained in the socket cavity.

* * * * *

UNITED STATES PATENT AND TRADEMARK OFFICE
CERTIFICATE OF CORRECTION

PATENT NO. : 6,974,484 B2 Page 1 of 1
DATED : December 13, 2005
INVENTOR(S) : Carl A. Caspers It is certified that error appears in the above-identified patent and that said Letters Patent is hereby corrected as shown below:

Title page,
Item [63], Related U.S. Application Data, after "Continuation of application No. 09/829,306, filed on Apr. 9, 2001, now abandoned, which is a continuation-in-part of application No. 09/325,297, filed on Jun. 3, 1999, now abandoned, and a continuation-in-part of application No. 09/534,274, filed on Mar. 23, 2000, now Pat. No. 6,554,868" insert -- which is a continuation-in-part of application No. 09/325,297, filed on Jun. 3, 1999, now abandoned --.

Signed and Sealed this

Ninth Day of May, 2006

JON W. DUDAS
*Director of the United States Patent and Trademark Office*